US010159333B2

(12) United States Patent
Moskovich et al.

(10) Patent No.: US 10,159,333 B2
(45) Date of Patent: Dec. 25, 2018

(54) PACKAGED ORAL CARE IMPLEMENT

(71) Applicant: COLGATE-PALMOLIVE COMPANY, New York, NY (US)

(72) Inventors: Robert Moskovich, East Brunswick, NJ (US); Alan Sorrentino, Cranbury, NJ (US); Yuanqiang Fang, Yangzhou (CN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/504,125

(22) PCT Filed: Aug. 15, 2014

(86) PCT No.: PCT/CN2014/084487
§ 371 (c)(1),
(2) Date: Feb. 15, 2017

(87) PCT Pub. No.: WO2016/023221
PCT Pub. Date: Feb. 18, 2016

(65) Prior Publication Data
US 2017/0238694 A1     Aug. 24, 2017

(51) Int. Cl.
*A46B 15/00*     (2006.01)
*B65D 75/36*     (2006.01)
(Continued)

(52) U.S. Cl.
CPC ........ *A46B 15/0093* (2013.01); *A61B 17/244* (2013.01); *B65D 25/205* (2013.01);
(Continued)

(58) Field of Classification Search
CPC .... A46B 15/0093; A46B 9/04; B65D 75/366; B65D 75/563; B65D 75/522;
(Continued)

(56) References Cited

U.S. PATENT DOCUMENTS 4,359,158 A     11/1982   Gringer
4,917,245 A  *  4/1990   Wu ..................... B65D 25/103
                                                     206/461
(Continued)

FOREIGN PATENT DOCUMENTS

EP         1 006 055        6/2000
JP       2014-114044        6/2014
(Continued)

OTHER PUBLICATIONS

International Search Report and the Written Opinion of the International Searching Authority issued in International Application PCT/CN2014/084487 dated May 13, 2015.

*Primary Examiner* — Robert Poon

(57) ABSTRACT

A packaged oral care implement that includes a package having a blister carton with a receiving trough, an insert tray positioned within the receiving trough, and a backer panel enclosing an open rear end of the receiving trough. The insert tray may be located within a middle axial section of the receiving trough and is in a fixed axial position relative to the blister carton through mating contact between a retaining section of the blister carton and a portion of the insert tray. An oral care implement is positioned within the receiving trough of the blister carton such that an an sate body of the oral care implement is positioned within a product receiving channel of the insert tray to prevent movement of the oral care implement relative to the insert tray.

15 Claims, 10 Drawing Sheets

(51) Int. Cl.
  *A61B 17/24* (2006.01)
  *B65D 25/20* (2006.01)
  *B65D 75/52* (2006.01)
  *B65D 75/56* (2006.01)
  *A46B 9/04* (2006.01)
  *A61C 17/22* (2006.01)

(52) U.S. Cl.
  CPC ......... *B65D 75/366* (2013.01); *B65D 75/522* (2013.01); *B65D 75/563* (2013.01); *A46B 9/04* (2013.01); *A61C 17/22* (2013.01)

(58) Field of Classification Search
  CPC .. B65D 75/324; B65D 75/326; B65D 75/368; B65D 75/367; B65D 75/36; B65D 75/323; B65D 75/322; A61C 19/02
  USPC .................. 206/461–462, 471, 806, 209, 361
  See application file for complete search history.

(56) References Cited

U.S. PATENT DOCUMENTS

| | | | |
|---|---|---|---|
| 5,154,293 A | 10/1992 | Gould | |
| 5,772,031 A * | 6/1998 | Landis | A61B 50/30 206/363 |
| D408,278 S | 4/1999 | Konop | |
| 7,475,775 B2 | 1/2009 | Fattori | |
| 7,854,320 B2 | 12/2010 | Greene et al. | |
| 9,516,936 B2 | 12/2016 | Nguyen | |
| 2006/0016704 A1 * | 1/2006 | Moskovich | B65D 73/0042 206/362.2 |
| 2007/0029223 A1 * | 2/2007 | Mazurek | B65D 73/0092 206/463 |
| 2009/0090643 A1 * | 4/2009 | Fischer | B65D 75/5833 206/361 |
| 2011/0100845 A1 | 5/2011 | Meech et al. | |
| 2012/0048760 A1 * | 3/2012 | Karey | A46B 15/0091 206/361 |
| 2012/0145567 A1 * | 6/2012 | Nguyen | B65D 75/326 206/63.5 |
| 2014/0021070 A1 | 1/2014 | Le | |
| 2014/0339111 A1 | 11/2014 | Moskovich et al. | |
| 2016/0207683 A1 | 7/2016 | Mokovich | |
| 2016/0297593 A1 | 10/2016 | Sorrentino | |

FOREIGN PATENT DOCUMENTS

| | | |
|---|---|---|
| WO | WO 1998/31605 | 7/1887 |
| WO | WO 2001/98171 | 12/2001 |

* cited by examiner

PACKAGED ORAL CARE IMPLEMENT

BACKGROUND

In the commercialization of oral care implements, such as toothbrushes, the current trend is to sell said oral care implements in sealed packages. In designing such packages, the following goals are often pursued: tampering prevention; visibility of the product and marketing information; distinguishing appearance relative to competitor packaging; structural stability to protect the oral care implement; and ease of opening. Often, these goals are competing and, thus, must be balanced. Thus, a need exists for an improved packaged oral care implement that more adequately achieves and/or balances one or more of the aforementioned goals.

BRIEF SUMMARY

The present invention is directed to a packaged oral care implement that includes a package having a blister carton with a receiving trough, an insert tray positioned within the receiving trough, and a backer panel enclosing an open rear end of the receiving trough. The insert tray is located within a middle axial section of the receiving trough and is in a fixed axial position relative to the blister carton through mating contact between a retaining section of the blister carton and a portion of the insert tray. An oral care implement is positioned within the receiving trough of the blister carton such that a body of the oral care implement is positioned within a product receiving channel of the insert tray to prevent movement of the oral care implement relative to the insert tray.

In one aspect, the invention can be a packaged oral care implement comprising: a package comprising: a blister carton comprising a receiving trough having an open rear end, the receiving trough extending along a longitudinal axis and comprising a lower axial section, a middle axial section, and an upper axial section, the middle axial section located between the lower and upper axial sections; an insert tray positioned within the receiving trough and located entirely within the middle axial section of the receiving trough, the insert tray retained in a fixed axial position relative to the blister carton through mating with a retaining section of the blister carton, the insert tray comprising a first product receiving channel; and a backer panel coupled to the blister carton that encloses the open rear end of the receiving trough; and a first oral care implement having an an sate body positioned within the receiving trough of the blister carton, a portion of the ansate body positioned within the first product receiving channel of the insert tray to prevent movement of the first oral care implement relative to the insert tray.

Optionally, the blister carton further comprises a plurality of sidewalls and a front wall that collectively define the receiving trough.

Optionally, the plurality of sidewalls comprises a first longitudinal sidewall and a second longitudinal sidewall, the retaining section of the blister carton comprises a first side retaining portion formed into the first longitudinal sidewall and a second side retaining portion formed into the second longitudinal sidewall; and the insert tray is at least partially retained in the fixed axial position by: (1) a first side portion of the insert tray mating with the first side retaining portion of the first longitudinal sidewall; and (2) a second side portion of the insert tray mating with the second side retaining portion of the second longitudinal sidewall.

Optionally, the first longitudinal sidewall comprises a first planar section and a second planar section, the first side retaining portion located between the first and second planar sections of the first longitudinal sidewall; and the second longitudinal sidewall comprises a first planar section and a second planar section, the second side retaining portion located between the first and second planar sections of the second longitudinal sidewall.

Optionally, the first side retaining portion of the first longitudinal sidewall comprises a first curved wall section having a concave inner surface and a convex outer surface, the first side portion of the insert tray nesting within the first curved wall section; and the second side retaining portion of the second longitudinal sidewall comprises a second curved wall section having a concave inner surface and a convex outer surface, the second side portion of the insert tray nesting within the second curved wall section.

Optionally, the convex outer surface of the first curved wall section outwardly protrudes from the first and second planar sections of the first longitudinal sidewall; and the convex outer surface of the second curved wall section outwardly protrudes from the first and second planar sections of the second longitudinal sidewall.

Optionally, the insert tray further comprises a middle portion located between the first and second side portions of the insert tray, the first product receiving channel located in the middle portion.

Optionally, the retaining section of the blister carton further comprises a front retaining portion formed into the front wall; and the insert tray is at least partially retained in the fixed axial position by the insert tray mating with the front retaining portion of the front wall.

Optionally, the front retaining portion comprises a detent in an inner surface of the front wall, a rear portion of the insert tray nesting within the detent.

Optionally, the package further comprises a label overlying the front retaining portion and at least partially concealing the insert tray.

Optionally, the front wall comprises a first planar section and a second planar section, the front retaining portion located between the first and second planar sections of the front wall.

Optionally, the package comprises a trapezoidal transverse cross-sectional profile and a trapezoidal longitudinal cross-sectional profile.

Optionally, no portion of the insert tray is visible when viewed from a front of the blister carton.

Optionally, the insert tray comprises an upper end and a lower end, the first product receiving channel extending between the upper and lower ends; wherein a middle portion of the ansate body is positioned within the first product receiving channel of the insert tray; and the ansate body comprises a proximal portion that extends beyond the lower end of the insert tray in a first axial direction and a distal portion that extends beyond the upper end of the insert tray in a second axial direction opposite the first axial direction.

Optionally, the backer panel is formed from an opaque cellulosic material, the blister carton is formed from a transparent plastic material, and the insert tray is formed of a transparent plastic material.

Optionally, the insert tray is located between the ansate body of the first oral care implement and the front wall of the blister carton.

Optionally, the ansate body comprises a head portion having a front surface from which a plurality of tooth cleaning elements extend; and the front surface of the head portion is oriented to face the front wall of the blister carton.

Optionally, a head portion of the ansate body of the first oral care implement is located entirely within the upper axial section of the receiving trough.

Optionally, the plurality of sidewalls comprises a first lateral sidewall that defines a closed upper end of the receiving trough and a second lateral sidewall that defines a closed lower end of the receiving trough.

Optionally, no portion of the ansate body of the first oral care implement contacts the front wall of the blister carton.

Optionally, no portion of the insert tray is located in the upper and lower axial sections of the receiving trough; and the middle axial section is less than 50% of a length of the receiving trough, the lower axial section is greater than 25% of the length of the receiving trough, and the upper axial section is greater than 25% of the length of the receiving trough.

In another aspect, the invention can be a packaged oral care implement comprising: a package comprising: a blister carton comprising a receiving trough having an open rear end, the receiving trough extending along a longitudinal axis; an insert tray positioned within the receiving trough, the insert tray comprising a first product receiving channel extending between upper and lower ends of the insert tray; and a backer panel coupled to the blister carton that encloses the open rear end of the receiving trough; and a first oral care implement comprising an ansate body positioned within the receiving trough of the blister carton, a middle portion of the ansate body of the first oral care implement positioned within the first product receiving channel of the insert tray so that a proximal portion of the ansate body extends beyond the lower end of the insert tray in a first axial direction and a distal portion of the ansate body extends beyond the upper end of the insert tray in a second axial direction opposite the first axial direction.

Optionally, the insert tray is retained in a fixed axial position relative to the blister carton through mating with a retaining section of the blister carton; and the ansate body is retained by the insert tray to prevent movement of the first oral care implement relative to the insert tray.

In yet another aspect, the invention can be a packaged oral care implement comprising: a package comprising: a carton comprising a receiving trough having an open rear end; an insert tray positioned within the receiving trough, the insert tray retained in a fixed axial position relative to the carton; and a backer panel coupled to the carton that encloses the open rear end of the receiving trough; and a first oral care implement having an ansate body positioned within the receiving trough of the carton, a portion of the ansate body positioned within a first product receiving channel of the insert tray to prevent movement of the first oral care implement relative to the insert tray; and wherein the insert tray is located between the ansate body and the carton.

Optionally, the carton is transparent.

Optionally, the carton further comprises a plurality of sidewalls and a front wall that collectively define the receiving trough, and the insert tray is located between the ansate body and the front wall of the carton.

Optionally, the insert tray is retained in the fixed axial position relative to the carton through mating with a retaining section of the carton.

Optionally, the plurality of sidewalls comprises a first longitudinal sidewall and a second longitudinal sidewall, the retaining section of the carton comprises a first side retaining portion formed into the first longitudinal sidewall and a second side retaining portion formed into the second longitudinal sidewall; and the insert tray is at least partially retained in the fixed axial position by: (1) a first side portion of the insert tray mating with the first side retaining portion of the first longitudinal sidewall; and (2) a second side portion of the insert tray mating with the second side retaining portion of the second longitudinal sidewall.

Optionally, the first longitudinal sidewall comprises a first planar section and a second planar section, the first side retaining portion located between the first and second planar sections of the first longitudinal sidewall; and the second longitudinal sidewall comprises a first planar section and a second planar section, the second side retaining portion located between the first and second planar sections of the second longitudinal sidewall Optionally, the first side retaining portion of the first longitudinal sidewall comprises a first curved wall section having a concave inner surface and a convex outer surface, the first side portion of the insert tray nesting within the first curved wall section; and the second side retaining portion of the second longitudinal sidewall comprises a second curved wall section having a concave inner surface and a convex outer surface, the second side portion of the insert tray nesting within the second curved wall section.

Optionally, the convex outer surface of the first curved wall section outwardly protrudes from the first and second planar sections of the first longitudinal sidewall; and the convex outer surface of the second curved wall section outwardly protrudes from the first and second planar sections of the second longitudinal sidewall.

Optionally, the insert tray comprises an upper end and a lower end, the first product receiving channel extending between the upper and lower ends; a first portion of the ansate body is positioned within the first product receiving channel of the insert tray; and the ansate body comprises a second portion that extends beyond the lower end of the insert tray in a first axial direction and a third portion that extends beyond the upper end of the insert tray in a second axial direction opposite the first axial direction.

Optionally, no portion of the ansate body of the first oral care implement contacts the carton.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
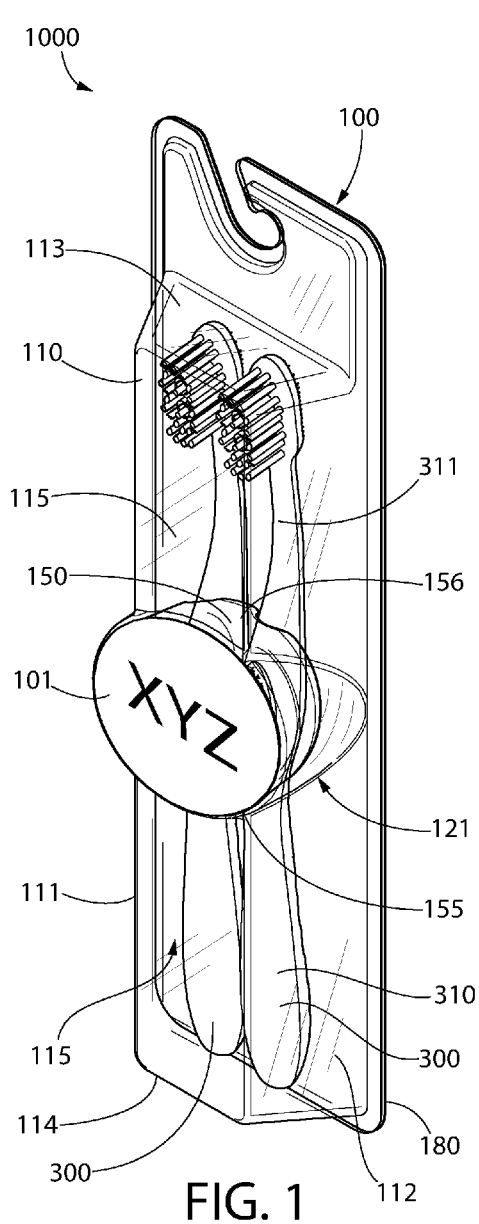
FIG. 1 is a front perspective view of a packaged oral care implement in accordance with a first embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Figure 2:
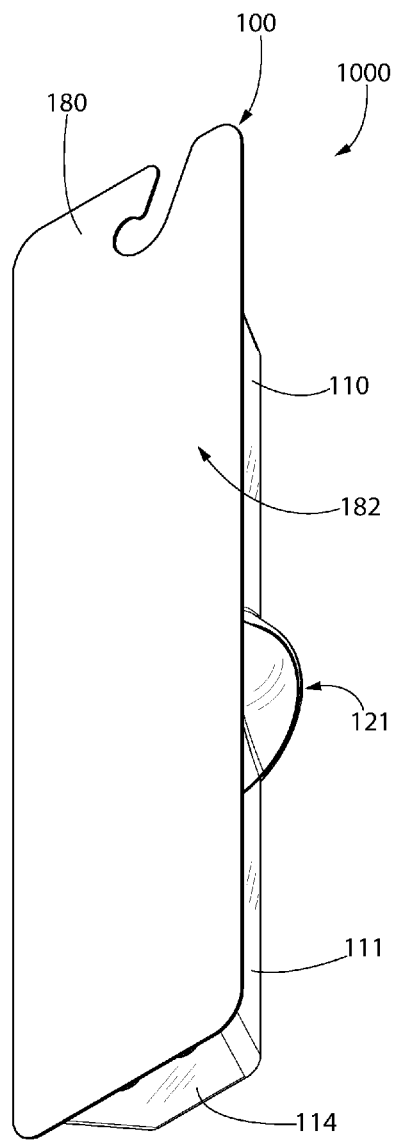
FIG. 2 is a rear perspective view of the packaged oral care implement of FIG. 1.
Figure 3:
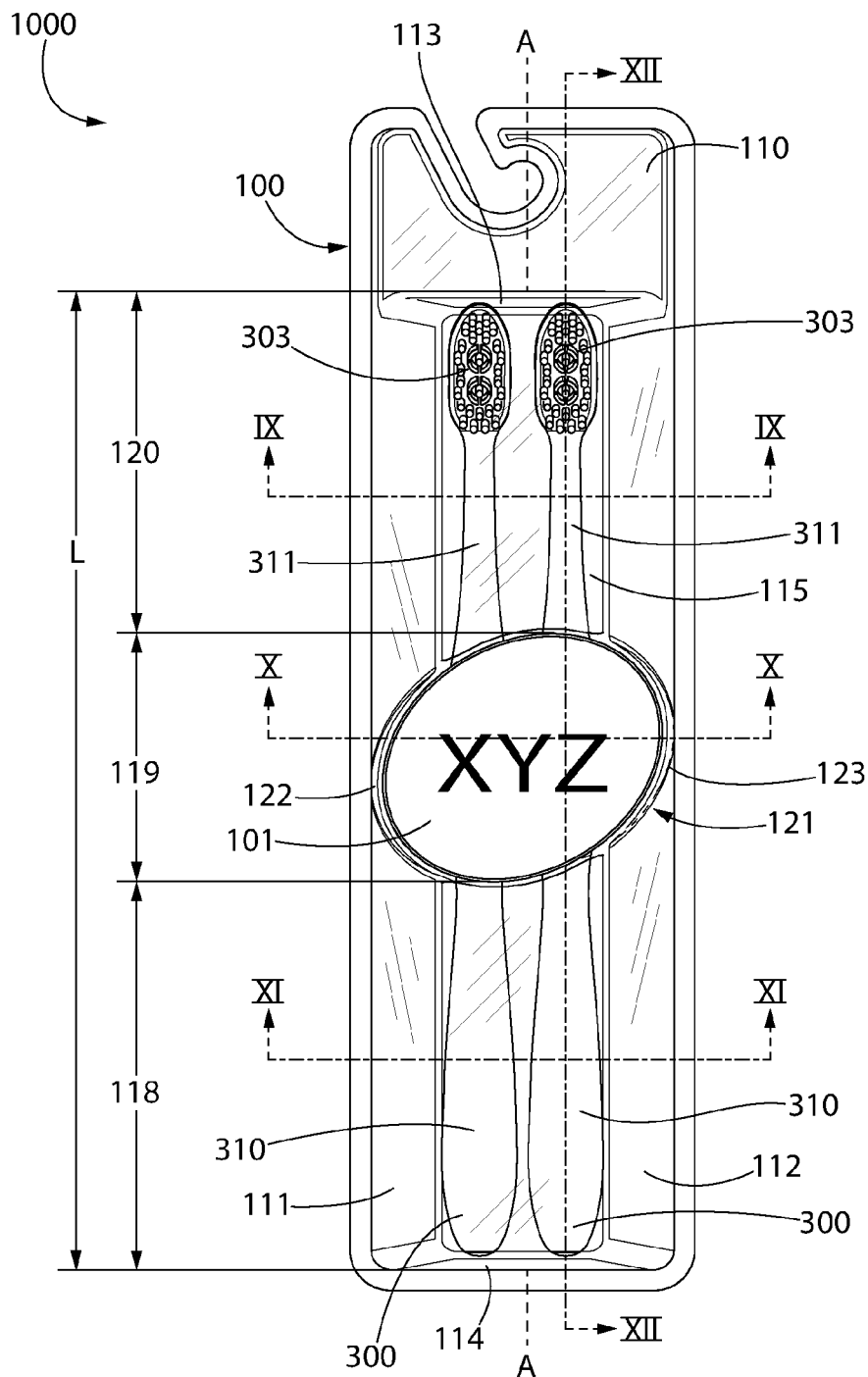
FIG. 3 is a front view of the packaged oral care implement of FIG. 1.

Referring first to FIGS. 1-4 concurrently, a packaged oral care implement 1000 will be described in accordance with one embodiment of the present invention. The packaged oral care implement 1000 generally comprises a package 100 and oral care implements 300. The package 100 houses the oral care implements 300 to present the oral care implements 300 for sale in a retail store and to protect the oral care implements 300 against damage during transport and other activities that take place prior to a consumer purchasing and using the oral care implements 300. Although two oral care implements 300 are depicted in the package 100 in the exemplified embodiment, a single oral care implement 300 or more than two oral care implements 300 may be positioned within the package 100 in other embodiments. The package 100 generally comprises a blister carton 110, an insert tray 150, and a backer panel 180. Furthermore, in the exemplified embodiment the package 100 also includes a label 101, although the label 101 may be omitted in certain other embodiments as desired. When the package 100 is fully assembled as depicted in FIGS. 1-3, the blister carton 110 and the backer panel 180 form a fully enclosed cavity within which the insert try 150 and the oral care implements 300 are positioned. The insert tray 150 is maintained within the blister carton 110 in a fixed axial position, and the insert tray 150 has channels that retain the oral care implements 300 so that the oral care implements 300 are held by the insert tray 150 in a fixed position. Each of the various components of the packaged oral care implement 1000 will be discussed in detail below.

Referring to FIGS. 1-6 concurrently, the blister carton 110 of the package 100 of the packaged oral care implement 1000 will be further described. In the exemplified embodiment, the blister carton 110 is formed of a transparent plastic material. Forming the blister carton 110 out of a transparent material may be desirable so that the oral care implements 300 contained therein are visible to a consumer for inspection prior to purchase. In certain embodiments the blister carton 110 may be referred to herein as a transparent carton. The blister carton 110 enables a consumer to view and inspect the oral care implements 300 contained within the package 1000 while preventing a consumer from touching the oral care implements 300 prior to purchase or prior to opening the package 1000 by separating the blister carton 110 from the backer panel 180 or otherwise. As used herein, the term transparent is not limited to materials that allow 100% of light to pass therethrough, but rather also includes translucent materials, materials that are tinted with a color while allowing some (or all) of the light to pass therethrough, or the like. Furthermore, in some embodiments only part of the blister carton 110 may be transparent while other parts of the blister carton 110 may not be transparent (i.e., opaque or the like). However, the use of a transparent material is preferable in certain embodiments so that a consumer can view the oral care implements positioned within the package 100 prior to purchase. In certain particular embodiments, the blister carton 110 is made from a formable web, such as a thermoformed plastic.

The blister carton 110 comprises a plurality of sidewalls including a first longitudinal sidewall 111, a second longitudinal sidewall 112, a first lateral sidewall 113 and a second lateral sidewall 114. In some embodiments, the plurality of sidewalls may be formed by a singular dome-shaped sidewall that can be conceptually divided into the first and second longitudinal sidewalls 111, 112 and the first and second lateral sidewalls 113, 114. The first and second longitudinal sidewalls 111, 112 have a length that is greater than a length of the first and second lateral sidewalls 113, and thus the blister carton 110 is elongated in the direction of extension of the first and second longitudinal sidewalls 111, 112. The blister carton 110 also comprises a front wall 115 that extends between each of the plurality of sidewalls 111, 112, 113, 114 and forms a closed front end of the blister carton 110. The plurality of sidewalls 111, 112, 113, 114 and the front wall 115 collectively define a receiving trough 116 within which the oral care implements 300 and the insert tray 150 are positioned when the package 100 is fully assembled. The first and second lateral sidewalls 113, 114 extend between the first and second longitudinal sidewalls 111, 112. Specifically, the first lateral sidewall 113 extends between the first and second longitudinal sidewalls 111, 112 at an upper region of the blister carton 110 to define a closed upper end of the receiving trough 116 and the second lateral sidewall 114 extends between the first and second longitudinal sidewalls 111, 112, at a lower region of the blister carton 110 to define a closed lower end of the receiving trough 116. The first and second longitudinal sidewalls 111, 112 define closed sides of the receiving trough 116 and the front wall 115 defines the closed front end of the receiving trough 116. The receiving trough 116 has an open rear end 117 that is closed in the assembled package 1000 due to coupling between the blister carton 110 and the backer panel 180.

The receiving trough 116 extends along a longitudinal axis A-A from the first lateral sidewall 113 to the second lateral sidewall 114. Furthermore, the receiving trough 116 comprises a lower axial section 118, a middle axial section 119, and an upper axial section 120. The lower axial section 118 extends from the second lateral sidewall 114 to the middle axial section 119 and the upper axial section 120 extends from the first lateral sidewall 113 to the middle axial section 119. Thus, the middle axial section 119 is located between the lower axial section 118 and the upper axial section 120. In the exemplified embodiment, the middle axial section 119 is located centrally between the lower and upper axial sections 118, 120 so as to be equidistant from each of the first and second lateral sidewalls 113, 114. However, the invention is not to be so limited in all embodiments and in certain other embodiments the middle axial section 119 may be located closer to the first lateral sidewall 113 than the second lateral sidewall 114, or the middle axial section 119 may be located closer to the second lateral sidewall 114 than the first lateral sidewall 113. Thus, the exact start and end points of each of the lower, middle, and upper axial sections 118, 119, 120 may be modified as desired.

The receiving trough 116 has a length L that includes each of the lower, middle, and upper axial sections 118, 119, 120. In certain embodiments, the middle axial section 119 of the receiving trough 116 is less than 50% of the length L of the receiving trough 116 and each of the lower and upper axial sections 118, 120 of the receiving trough 116 is greater than 25% of the length L of the receiving trough 116. In certain embodiments, the middle axial section 119 of the receiving trough 116 is less than 40% of the length L of the receiving trough 116, in other embodiments the middle axial section 119 of the receiving trough 116 is less than 35% of the length L of the receiving trough 116, and in still other embodiments the middle axial section 119 of the receiving trough 116 is less than 30% of the length L of the receiving trough 116. The lower and upper axial sections 118, 120 make up the remaining percentage of the length L of the receiving trough 116, although the percentage of the length L of the receiving trough 116 that is formed by each of the lower and upper axial sections 118, 120 need not be the same in all embodiments (although it can be the same in some embodiments).

Furthermore, as will be discussed in more detail below, in certain embodiments the entirety of the insert tray 150 is located within the middle axial section 119 of the receiving trough 116 such that no portion of the insert tray 150 is located within either of the upper or lower axial sections 118, 120 of the receiving trough 116. Thus, the insert tray 150 takes up less than 50% of the axial length L of the receiving trough 116, or less than 40% of the axial length L of the receiving trough 116, or less than 35% of the axial length L of the receiving trough 116, or less than 30% of the axial length L of the receiving trough 116. Maintaining the insert tray 150 to have a small axial length relative to the axial length L of the receiving trough 116 prevents the insert tray 150 from blocking a large amount of text or graphics that may be provided on the backer panel 180 while the insert tray 150 is still able to retain the oral care implements 300 in a desired position and orientation within the receiving trough 116. Specifically, even though the insert tray 150 may be transparent as discussed below, having extra layers of transparent plastic may blur graphics, instructions, and other text provided on the backer panel 180. Minimizing the axial length of the insert tray 150 minimizes the amount of text, graphics, and/or instructions that may be blurred or otherwise blocked by the insert tray 150.

Referring briefly to FIGS. 1-4, 9, and 12, each of the first and second longitudinal sidewalls 111, 112 extends from the front wall 115 towards the open rear end 117 at a non-normal or oblique angle. More specifically, each of the first and second longitudinal sidewalls 111, 112 extends from the front wall 115 at a first obtuse angle $\ominus 1$. Similarly, each of the first and second lateral sidewalls 113, 114 extends from the front wall 115 towards the open rear end 117 at a non-normal or oblique angle. More specifically, each of the first and second lateral sidewalls 113, 114 extends from the front wall 115 at a second obtuse angle $\ominus 2$. In the exemplified embodiment, the first obtuse angles $\ominus 1$ formed between the first and second longitudinal sidewalls 111, 112 and the front wall 115 are greater than the second obtuse angles $\ominus 2$ formed between the first and second lateral sidewalls 113, 114 and the front wall 115. Specifically, the first obtuse angle $\ominus 1$ may be between 100° and 140°, more specifically between 110° and 130°, still more specifically between 115° and 125°, and still more specifically approximately 120°. The second obtuse angle may be between 91° and 99° more specifically between 93° and 97°, and still more specifically approximately between 94° and 96°. Of course, angles outside of the above-noted ranges can also be used in other embodiments, and in certain embodiments $\ominus 2$ may be approximately 90°. In the exemplified embodiment, due to the angles between the first and second longitudinal sidewalls 111, 112 and the front wall 115 and between the first and second lateral sidewalls 113, 114 and the front wall 115, the blister carton 110 (and the package 100 as a whole) comprises a trapezoidal transverse cross-sectional profile (see FIG. 9) and a trapezoidal longitudinal cross-sectional profile (see FIG. 12). In certain other embodiments, the blister carton 110 may comprise a trapezoidal transverse cross-sectional profile and a rectangular longitudinal cross-sectional profile (such as when $\ominus 2$ is approximately 90°).

Referring again to FIGS. 1-6 concurrently, the blister carton 110 will be further described. The blister carton 110 comprises a retaining section 121 that mates with the insert tray 150 to retain the insert tray 150 in a fixed axial position within the receiving trough 116. In the exemplified embodiment, the retaining section 121 is located within the middle axial section 119 of the receiving trough 116, and it is the location of the retaining section 121 that defines the upper and lower axial bounds of the middle axial section 119 of the receiving trough 116. The retaining section 121 comprises a first side retaining section 122 formed into the first longitudinal sidewall 111 and a second side retaining section 123 formed into the second longitudinal sidewall 112. The first and second side retaining portions 122, 123 mate with corresponding portions of the insert tray 150 to retain the insert tray 150 in the receiving trough 116. Specifically, the shape of the insert tray 150 is duplicated in the retaining section 121 of the blister carton 110 to lock the insert tray 150 into a desired position within the insert tray 150. The mating between the insert tray 150 and the retaining section 121 of the blister carton 110 will be discussed in more detail below.

The first longitudinal sidewall 111 of the blister carton 110 comprises a first planar section 124, a second planar section 125, and the first side retaining portion 122. The first and second planar sections 124, 125 are oriented at an oblique angle relative to a horizontal plane that includes the front face 115 of the blister carton 110 and the first side retaining portion 122 is oriented at a substantially perpendicular angle relative to the same horizontal plane that includes the front face 115 of the blister carton 110 (substantially perpendicular being plus or minus 5° from perpendicular). The first planar section 124 of the first longitudinal sidewall 111 extends from the first lateral sidewall 113 to the first side retaining portion 122 and the second planar section 125 of the first longitudinal sidewall 111 extends from the second lateral sidewall 114 to the first side retaining portion 122. Thus, the first side retaining portion 122 is located between the first and second planar sections 124, 125 of the first longitudinal sidewall 111 in the middle axial section 119 of the blister carton 110. The first and second planar sections 124, 125 of the first longitudinal sidewall 111 are planar (although angled as noted above), and in the exemplified embodiment they extend along the same plane (although they could extend along different planes by being formed at different angles from the front wall 115 in other embodiments).

The first side retaining portion 122 comprises a first curved wall section 126 of the first longitudinal sidewall 111 that extends between the first and second planar sections 124, 125 of the first longitudinal sidewall 111. The first curved wall section 126 essentially forms a curved bulge, bump, or protrusion in the first longitudinal sidewall 111 between the first and second planar sections 124, 125 of the first longitudinal sidewall 111. Thus, the first curved wall section 126 of the first longitudinal sidewall 111 has a concave inner surface 141 and a convex outer surface 142 (see FIGS. 5, 6, and 10). The convex outer surface 142 of the first curved wall section 126 outwardly protrudes from and extends laterally beyond outer surfaces 145 of the first and second planar sections 124, 125 of the first longitudinal sidewall 111. Thus, the first longitudinal sidewall 111 has the first and second planar sections 124, 125 that are axially spaced apart from one another and connected by the first curved wall section 126.

The second longitudinal sidewall 112 of the blister carton 110 comprises a first planar section 127, a second planar section 128, and the second side retaining portion 123. The first and second planar sections 127, 128 are oriented at an oblique angle relative to a horizontal plane that includes the front face 115 of the blister carton 110 and the second side retaining portion 123 is oriented at a substantially perpendicular angle relative to the same horizontal plane that includes the front face 115 of the blister carton 110 (substantially perpendicular being plus or minus 5° from perpendicular). The first planar section 127 of the second longitudinal sidewall 112 extends from the first lateral sidewall 113 to the second side retaining portion 123 and the second planar section 128 of the second longitudinal sidewall 112 extends from the second lateral sidewall 114 to the second side retaining portion 123. Thus, the second side retaining portion 123 is located between the first and second planar sections 127, 128 of the second longitudinal sidewall 112. The first and second planar sections 127, 128 of the second longitudinal sidewall 112 are planar (although angled as noted above), and in the exemplified embodiment they extend along the same plane (although they could extend along different planes by being formed at different angles from the front wall 115 in other embodiments).

The second side retaining portion 123 comprises a second curved wall section 129 of the second longitudinal sidewall 112 that extends between the first and second planar sections 127, 128 of the second longitudinal sidewall 112. The second curved wall section 129 essentially forms a curved bulge, bump, or protrusion in the second longitudinal sidewall 112 between the first and second planar sections 127, 128 of the second longitudinal sidewall 112. Thus, the second curved wall section 129 of the second longitudinal sidewall 112 has a concave inner surface 143 and a convex outer surface 144 (see FIGS. 5, 6, and 10). The convex outer surface 144 of the second curved wall section 129 outwardly protrudes from and extends laterally beyond outer surfaces 146 of the first and second planar sections 127, 128 of the second longitudinal sidewall 112. Thus, the second longitudinal sidewall 112 has the first and second planar sections 127, 128 that are axially spaced apart from one another and connected by the second curved wall section 129.

The retaining section 121 of the blister carton 110 also comprises a front retaining portion 130 that is formed into the front wall 115 of the blister carton 110. The front retaining portion 130 comprises a detent 139 that is formed into the inner surface of the front wall 115. The detent 139 forms a slight protrusion in the front wall 115, which forms the front retaining portion 130. The detent 139 substantially conforms in size and shape to the size and shape of the insert tray 150 to securely retain the insert tray 150 in the retaining section 121 of the blister carton 110 as discussed in more detail below. The front wall 115 of the blister carton 110 has a first planar section 131 that extends from the first lateral sidewall 113 to the retaining section 121 and a second planar section 132 that extends from the second lateral sidewall 114 to the retaining section 121. In the exemplified embodiment, the first and second planar sections 131, 132 of the front wall 115 are in plane with one another, although in other embodiments they can be out of plane. The retaining section 121, and more specifically the front retaining portion 130 of the retaining section 121, is located axially between the first and second planar sections 131, 132 of the front wall 115. In certain embodiments, the front retaining portion 130 of the retaining section 121 is planar but slightly elevated relative to the first and second planar sections 131, 132 of the front wall 115 such that the front retaining portion 130 of the front wall 115 is out of plane with or offset in elevation relative to the first and second planar sections 131, 132 of the front wall 115.

Thus, as noted above, the front retaining portion 130 of the retaining section 121 forms a portion of the front wall 115 of the blister carton 110, the first side retaining portion 122 of the retaining section 121 forms a portion of the first longitudinal sidewall 111 of the blister carton 110, and the second side retaining portion 123 of the retaining section 121 forms a portion of the second longitudinal sidewall 112 of the blister carton 110. In the exemplified embodiment, the front retaining portion 130 of the retaining section 121 is centrally located between the first and second lateral walls 113, 114, although the invention is not to be so limited in all embodiments and the front retaining portion 130 of the retaining section 121 can be positioned at any location along the front wall 115 of the blister carton 110. In the exemplified embodiment, the front retaining portion 130 is oval in shape, although the invention is not to be so limited and other polygonal shapes can be used for the front retaining portion 130. The front retaining portion 130 has a flat, planar surface so that the label 101 can be easily attached to the front retaining portion 130 as desired.

The oval shape of the front retaining portion 130 is achieved due to the first and second side retaining portions 122, 123 protruding beyond the outer surfaces of the first and second longitudinal sidewalls 111, 112, respectively. Specifically, the front wall 115 of the blister carton 110 is generally in the shape of an axially elongated rectangle. Because the first and second side retaining portions 122, 123 protrude outward from the first and second longitudinal sidewalls 111, 112, the front retaining portion 130 is able to form a surface that extends beyond the outer surfaces 145, 146 of the first and second longitudinal sidewalls 111, 112 at least at the location where the first and second longitudinal sidewalls 111, 112 intersect the front wall 115. This enables the front retaining portion 130 to have an added surface area for having the label 101 (which may be a sticker or the like) positioned thereon.

The oval shape of the front retaining portion 130 is oriented so as to not be aligned along an axis transverse to the longitudinal axis A-A. Specifically, in the exemplified embodiment the first curved wall section 126 and the second curved wall section 129 are not positioned at the same location along the length of the blister carton 110 and are not aligned along an axis transverse to the longitudinal axis A-A. In the exemplified embodiment, the first curved wall section 126 is positioned closer to the second lateral sidewall 114 than it is to the first lateral sidewall 113 and the second curved wall section 129 is positioned closer to the first lateral sidewall 113 than it is to the second lateral sidewall 114. Thus, the first curved wall section 126 is positioned closer to the second lateral sidewall 114 than the second curved wall section 129 and the second curved wall section 129 is positioned closer to the first lateral sidewall 113 than the first curved wall section 126. This results in the oval shape (i.e., egg shape) of the front retaining portion 130 having an orientation so as to appear tilted in a direction from the second lateral sidewall 114 to the first lateral sidewall 113 as it extends from the first longitudinal sidewall 111 to the second longitudinal sidewall 112.

In embodiments that use the label 101, the label 101 may include text, graphics, instructions, or the like to provide information about the oral care implements 300 contained within the package 100 or its manufacturer to a consumer. The label 101 may have a size and shape (and surface area) that is substantially identical to the size and shape (and surface area) of the front retaining portion 130 such that the front retaining portion 130 may form a label receiving surface of the blister carton 110. Alternatively, the label 101 may have a greater or smaller surface area than the surface area of the front retaining portion 130 and may have a shape that is different than the shape of the front retaining portion 130 in other embodiments. As will be appreciated from the discussion below, the insert tray 150 is positioned within the blister carton 110 below the front retaining portion 130. Thus, placing the label 101 (which may be opaque) on the front retaining portion 130 will block a consumer's view of the insert tray 150, which results in an aesthetic in which the oral care implements 300 appear to be floating within the receiving trough 116 of the package 100.

Referring now to FIGS. 1, 4, 7, and 8 concurrently, the insert tray 150 of the package 100 will be further described. In certain embodiments, the insert tray 150 is formed of a transparent plastic material. However, the invention is not to be so limited in all embodiments and the insert tray 150 may be formed of translucent plastic materials, opaque plastic materials, or non-plastic materials including rubbers, elastomers, or the like. However, the insert tray 150 is preferably formed of a lightweight plastic material, such as a thermoformed plastic.

As noted above, the insert tray 150 has a size and shape that permits the insert tray 150 to be retained within the receiving trough 116 in a fixed axial location. Furthermore, the insert tray 150 has a shape and contour that enables the insert tray 150 to retain the oral care implements 300 in a desired position within the receiving trough 116. In the exemplified embodiment, the insert tray 150 has a front surface 151, an opposing rear surface 152, a first side portion 153 and an opposing second side portion 154 extending between the front and rear surfaces 151, 152, and an upper end 155 and an opposing lower end 156 extending between the front and rear surfaces 151, 152. The first and second side portions 153, 154 and the upper and lower ends 155, 156 collectively form the outer surface of the insert tray 150, which in the exemplified embodiment is oval in shape and corresponds in shape to the retaining section 121 of the blister carton 110. The insert tray 150 also has a middle portion 159 located between the first and second side portions 153, 154.

In the exemplified embodiment, a first product receiving channel 157 and a second product receiving channel 158 are formed into the insert tray 150 and extend along the length of the insert tray 150 from the upper end 155 of the insert tray 150 to the lower end 156 of the insert tray 150. More specifically, each of the first and second product receiving channels 157 is located in the middle portion 159 of the insert tray 150 between the first and second side portions 153, 154 of the insert tray. Each of the first and second product receiving channels 157, 158 is a groove, indent, depression, or recess that is formed into the front surface 151 of the insert tray 150. Furthermore, each of the first and second product receiving channels 157, 158 is configured (by size and shape) to receive and retain a portion of one of the oral care implements 300. Although described and illustrated herein with two product receiving channels 157, 158, the invention is not to be so limited and the insert tray 150 may only include a single product receiving channel or more than two product receiving channels in other embodiments depending on the number of oral care implements that are desired to be retained within the package 100.

Referring to FIGS. 1, 4, 7, 8, and 10 concurrently, the positioning of the insert tray 150 within the receiving trough 116 will be described. As noted above, the insert tray 150 is retained in a fixed axial position relative to the blister carton 110 through mating between the outer surfaces of the insert tray 150 and the retaining section 121 of the blister carton 110. Thus, the insert tray 150 fits entirely within the retaining section 121 of the blister carton 110 (which is located in the middle axial section 119 of the blister carton 110) and is prevented from axial movement within the blister carton 110 due to the corresponding shapes of the retaining section 121 and the outer surface of the insert tray 150. More specifically, in the exemplified embodiment the insert tray 150 is at least partially retained in the fixed axial position by the first side portion 153 of the insert tray 150 mating with the first side retaining portion 122 of the first longitudinal sidewall 111 of the blister carton 110 and by the second side portion 154 of the insert tray 150 mating with the second side retaining portion 123 of the second longitudinal sidewall 112 of the blister carton 110.

Specifically, when the insert tray 150 is positioned within the retaining section 121 of the blister carton 110, the first and second side portions 153, 154 of the insert tray 150 protrude beyond the planar sections 124, 125, 127, 128 of the first and second longitudinal sidewalls 111, 112 and nest within the area of the receiving trough 116 defined by the first and second curved wall sections 126, 129 of the first and second longitudinal sidewalls 111, 112. Thus, axial movement of the insert tray 150 is prevented because the first and second side portions 153, 154 of the insert tray 150 are trapped between the first and second planar sections 124, 125 of the first longitudinal sidewall 111 and the first and second planar sections 127, 128 of the second longitudinal sidewall 112. The portions of the insert tray 150 that are positioned within the area defined by the first and second curved wall sections 126, 129 of the first and second longitudinal sidewalls 111, 112 are abutted against/positioned between the first and second planar sections 124, 125, 127, 128 of the first and second longitudinal sidewalls 111, 112, which prevents axial movement of the insert tray 150 as noted herein (even if some axial movement is permitted, it is a very small amount and is limited by the difference between the axial length of the first and second curved walls 126, 129 and the axial length of the insert tray 150). Stated another way, due to the outwardly bulging structure of the first and second curved wall sections 126, 129 of the first and second longitudinal sidewalls 111, 112 relative to the first and second planar sections 124, 125, 127, 128 of the first and second longitudinal sidewalls 111, 112, axial movement of the insert tray 150 is prevented when the insert tray 150 is positioned within the retaining section 121 of the blister carton 110.

Figure 10:
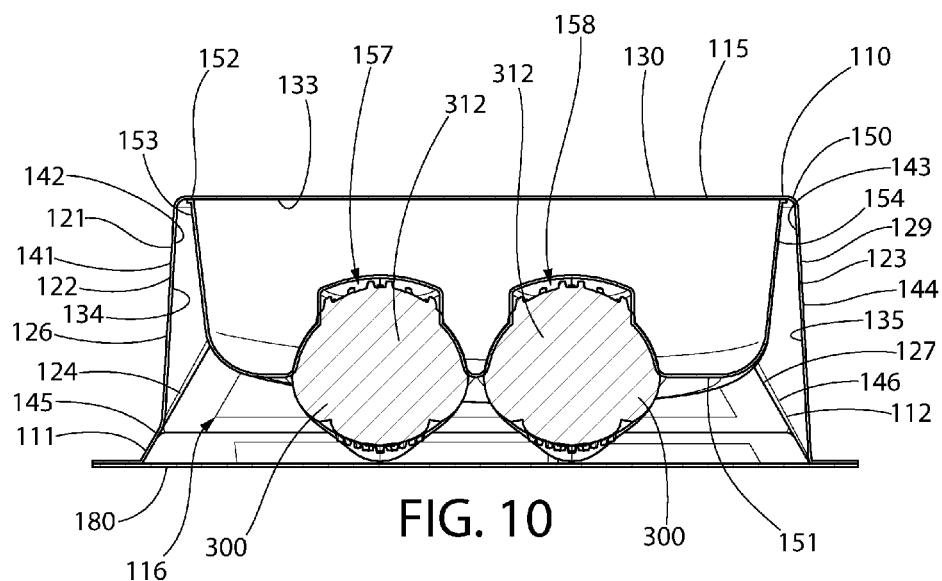
FIG. 10 is a cross-sectional view taken along line X-X of FIG. 3.
Figure 11:
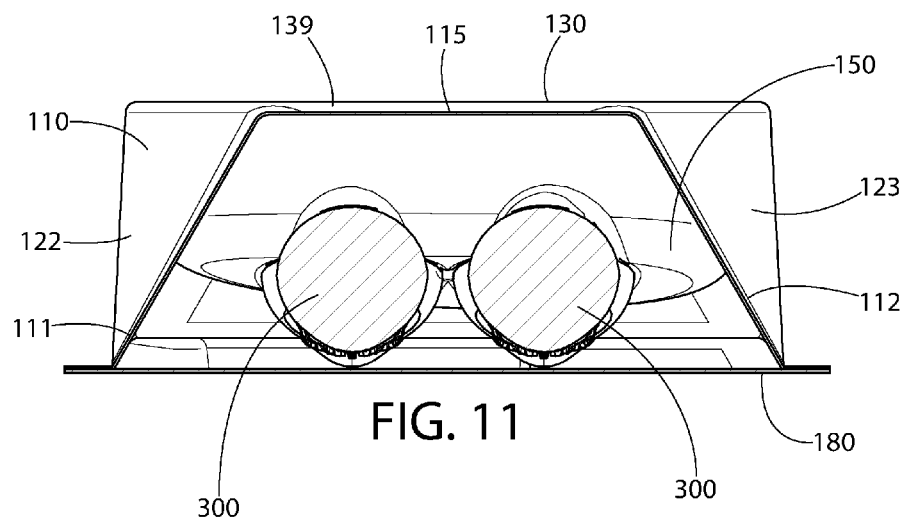
FIG. 11 is a cross-sectional view taken along line XI-XI of FIG. 3.
Figure 12:
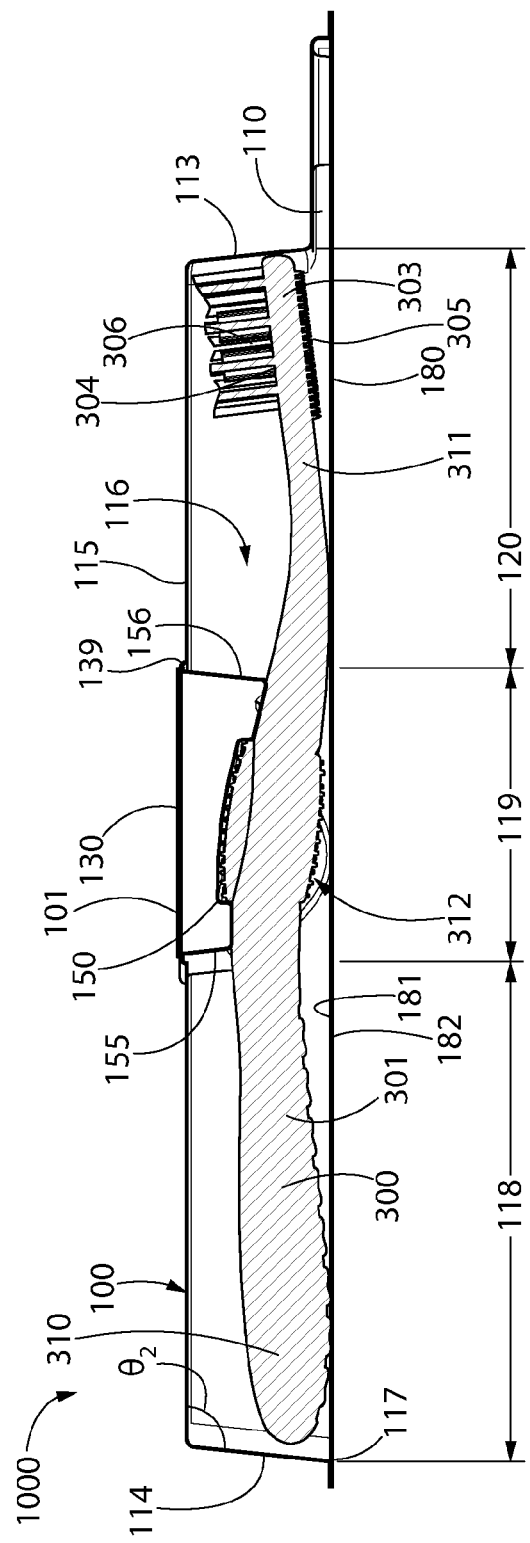
FIG. 12 is a cross-sectional view taken alone line XII-XII of FIG. 3.

In the assembled package 100, the insert tray 150 is positioned within the retaining section 121 of the blister carton 110 so that the rear surface 152 of the insert tray 150 is adjacent to an inner surface 133 of the front retaining portion 130 of the retaining section 121 and the front surface 151 of the insert tray 150 is facing the open rear end 117 of the blister carton 110. As depicted in FIG. 10, in certain embodiments the rear surface 152 of the insert tray 150 may be in surface contact with the inner surface 133 of the front retaining portion 130 of the retaining section 121. Thus, when the insert tray 150 is positioned within the retaining section 121 of the blister carton 110, each of the product receiving channels 157, 158 is facing away from the front wall 115 of the blister carton 110 and towards the open rear end 117 of the blister carton 110.

In the exemplified embodiment, the first side portion 153 of the insert tray 150 is adjacent to and spaced apart from an inner surface 134 of the first side retaining portion 122 of the first longitudinal wall 111 (i.e., the concave inner surface 142 of the first curved wall 122) and the second side portion 154 of the insert tray 150 is adjacent to and spaced apart from an inner surface 135 of the second side retaining portion 123 of the second longitudinal wall 112 (i.e., the concave inner surface 143 of the second curved wall 123). However, the invention is not to be so limited in all embodiments and in certain other embodiments the first side portion 153 of the insert tray 150 may be in surface contact with the inner surface 134 of the first side retaining portion 122 and the second side portion 154 of the insert tray 150 may be in surface contact with the inner surface 135 of the second side retaining portion 123.

Regardless of whether there is surface contact between the first and second side portions 153, 154 of the insert tray 150 and the first and second side retaining portions 122, 123 of the first and second longitudinal walls 111, 112, as can be seen in FIG. 10 the first and second side portions 153, 154 of the insert tray 150 extend laterally beyond the planar portions 124, 125, 127, 128 of the first and second longitudinal walls 111, 112 so that axial movement of the insert tray 150 within the receiving trough 116 is prevented/minimized. Thus, the first side portion 153 of the insert tray 150 nests within the first curved wall section 126 of the first longitudinal wall 111 and the second side portion 154 of the insert tray 150 nests within the second curved wall section 129 of the second longitudinal wall 112. Furthermore, the insert tray 1560 is at least partially retained in the fixed axial position by the insert tray 150 mating with the front retaining portion 130 of the front wall 115 such that a rear portion of the insert tray 150 that includes the rear surface 152 nests within the detent 139 in the front wall 115.

Due to the oval shape of the retaining section 121 of the blister carton 110 and of the insert tray 150, in the exemplified embodiment the insert tray 150 must be rotated relative to the blister carton 110 prior to inserting the insert tray 150 into the blister carton 110 to ensure that the shapes of the insert tray 150 and retaining section 121 are aligned. However, if the shapes are circular instead of ovular, such rotational alignment may not be required. In the exemplified embodiment, when proper rotational alignment between the insert tray 150 and the retaining section 121 of the blister carton 110 is achieved, the first and second product receiving channels 157, 158 of the insert tray 150 are oriented so as to be parallel with the longitudinal axis A-A of the receiving trough 116. This enables the first and second product receiving channels 157, 158 of the insert tray 150 to be used to retain the oral care implements 300 within the receiving trough 116.

Figure 4:
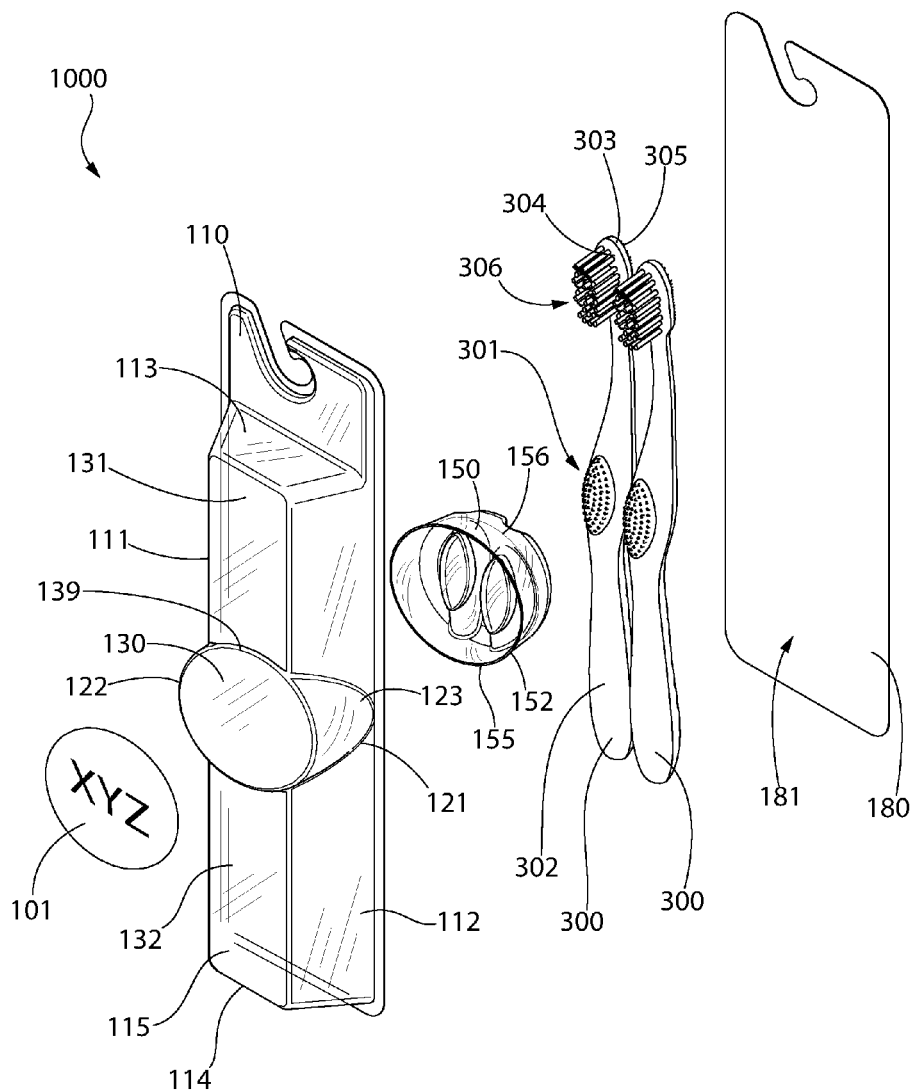
FIG. 4 is an exploded view of the packaged oral care implement of FIG. 1 illustrating a blister carton, an insert tray, oral care implements, a backer panel, and a label.
Figure 5:
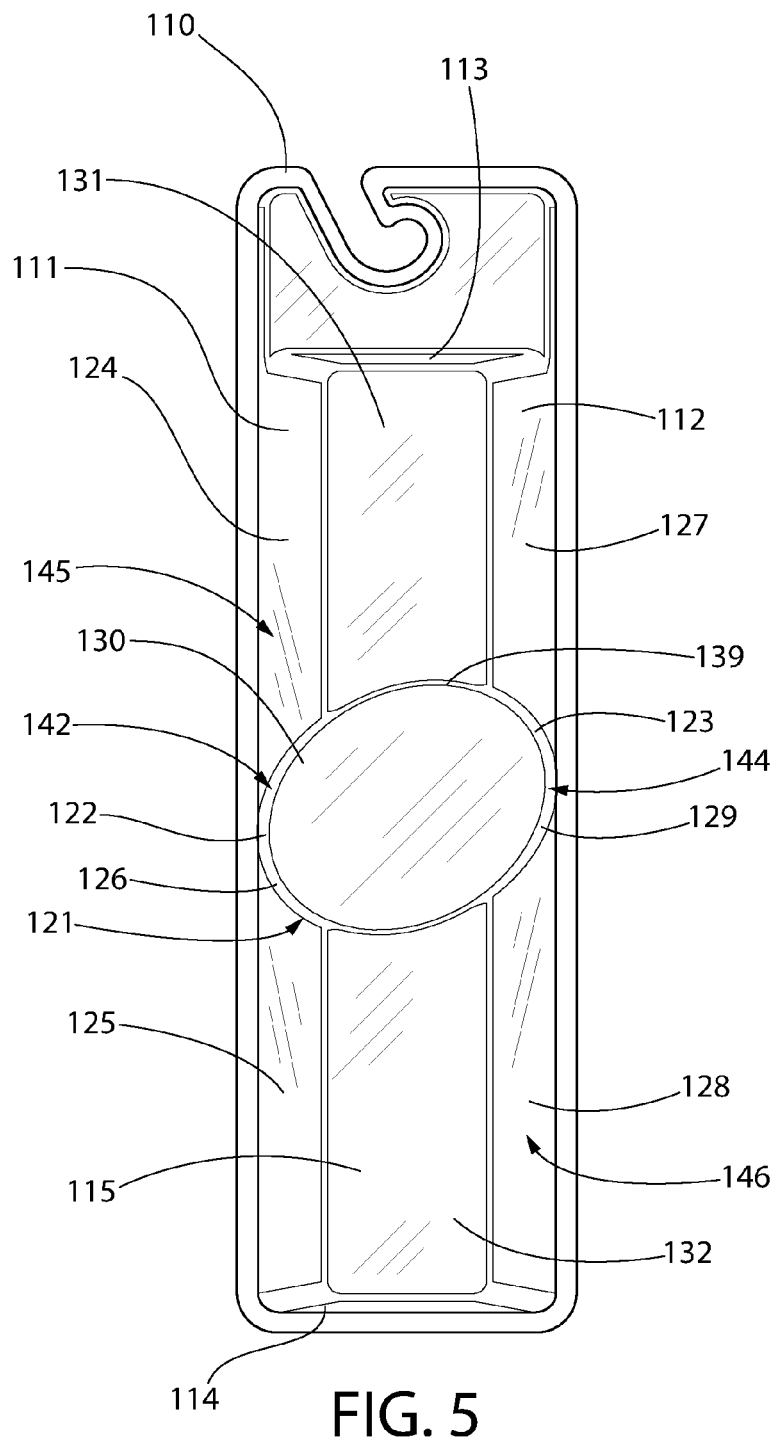
FIG. 5 is a front view of the blister carton of the packaged oral care implement of FIG. 1.
Figure 6:
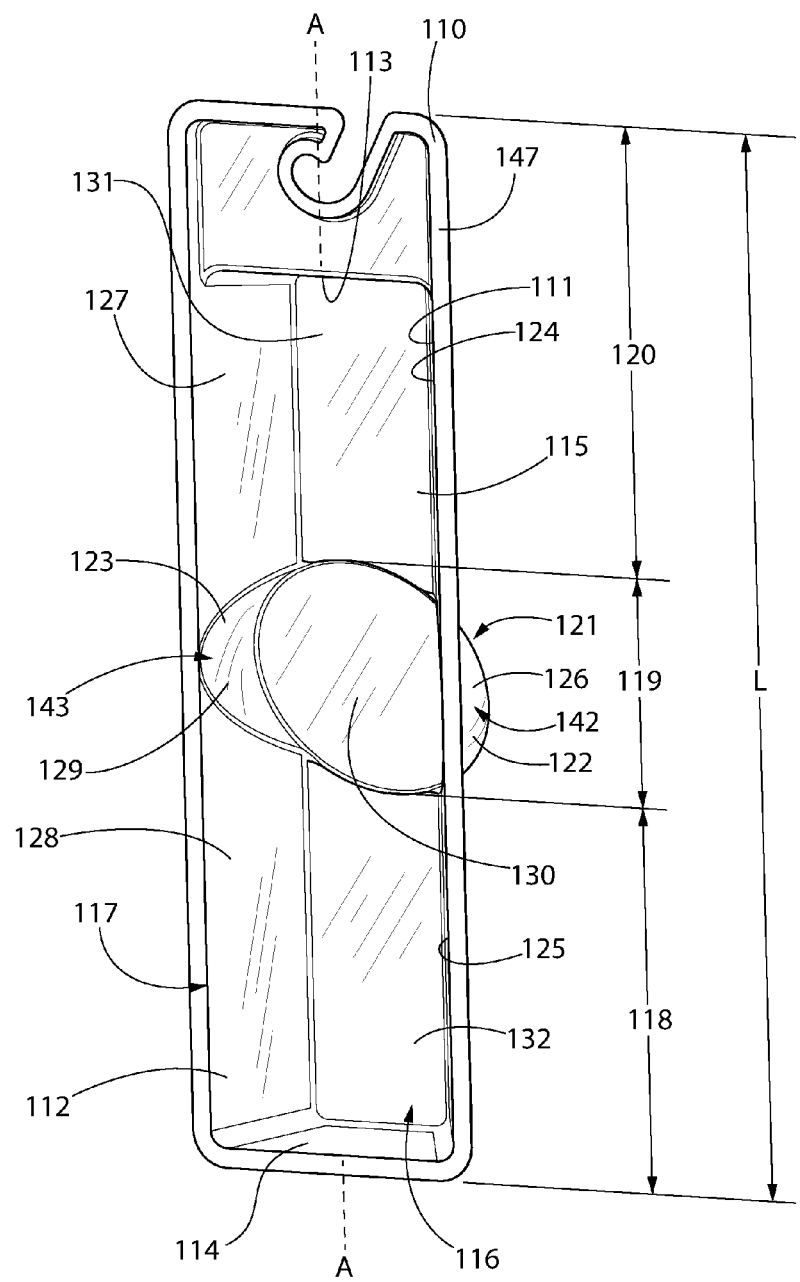
FIG. 6 is a rear perspective view of the blister carton of FIG. 5.
Figure 7:
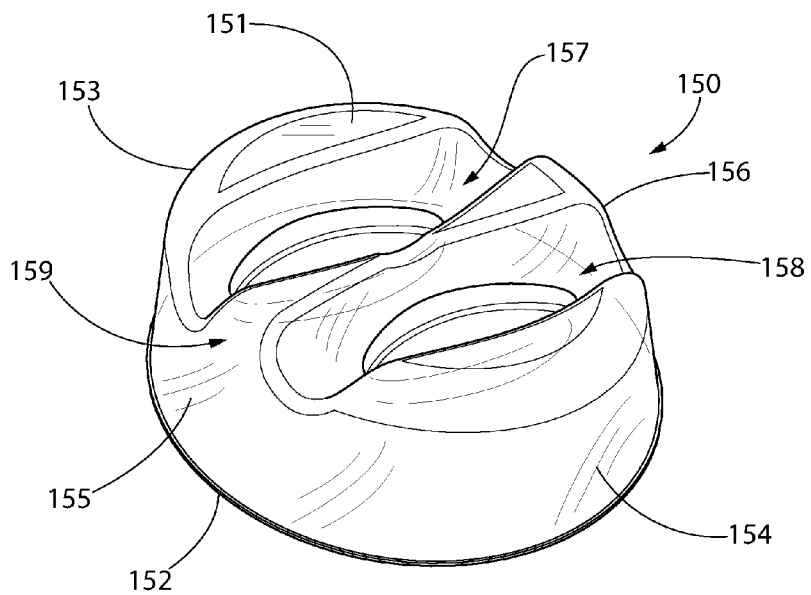
FIG. 7 is a front perspective view of the insert tray of the packaged oral care implement of FIG. 1.
Figure 8:
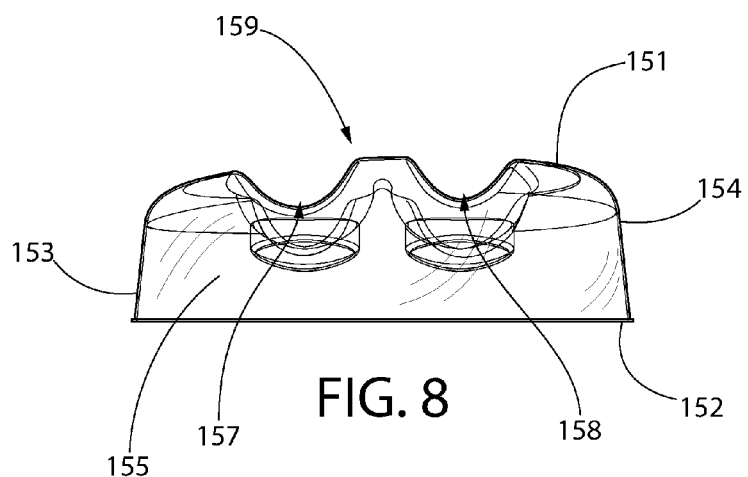
FIG. 8 is a top view of the insert tray of FIG. 7.
Figure 9:
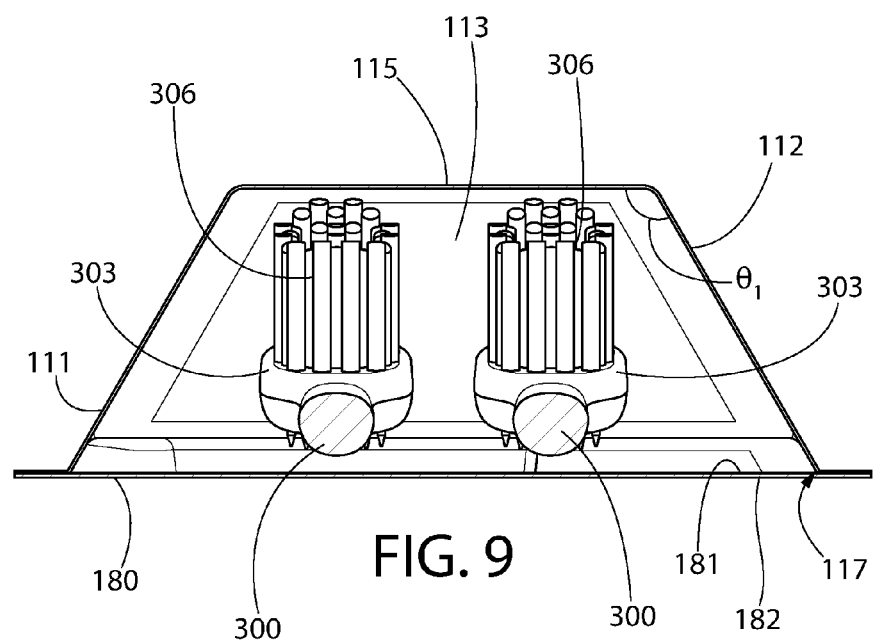
FIG. 9 is a cross-sectional view taken along line IX-IX of FIG. 3.

Referring briefly to FIGS. 1, 3, and 4 concurrently, the oral care implements 300 will be described. In the exemplified embodiment, the oral care implements 300 are in the form of a manual toothbrush. However, in certain other embodiments the oral care implements 300 can take on other forms such as being a powered toothbrush, a tongue scraper, a gum and soft tissue cleanser, a water pick, an interdental device, a tooth polisher, a specially designed ansate implement having tooth engaging elements or any other type of implement that is commonly used for oral care. Furthermore, in some embodiments that include more than one of the oral care implements 300, each of the oral care implements 300 may be a different type of oral care implement (such as one manual toothbrush and one interdental device, or the like). Thus, it is to be understood that the inventive concepts discussed herein can be applied to any type of oral care implement unless a specific type of oral care implement is specified in the claims.

In the exemplified embodiment, the oral care implements 300 generally comprise an ansate body 301. The ansate body 301 generally comprises a handle 302 and a head 303 that is attached to the handle 302. The handle 302 is an elongated structure that provides the mechanism by which the user can hold and manipulate the oral care implement 300 during use. In the exemplified embodiment, the handle 302 is generically depicted having various contours for user comfort. Of course, the invention is not to be limited by the specific shape illustrated for the handle 302 in all embodiments and in certain other embodiments the handle 302 can take on a wide variety of shapes, contours, and configurations, none of which are limiting of the present invention unless so specified in the claims.

In the exemplified embodiment, the handle 302 is formed of a rigid plastic material, such as for example without limitation polymers and copolymers of ethylene, propylene, butadiene, vinyl compounds, and polyesters such as polyethylene terephthalate. Of course, the invention is not to be so limited in all embodiments and the handle 302 may include a resilient material, such as a thermoplastic elastomer, as a grip cover that is molded over portions of or the entirety of the handle 302 to enhance the gripability of the handle 302 during use. Such a resilient material is illustrated as a thumb grip on the handle 302. Furthermore, in other embodiments portions of the handle 302 that are typically gripped by a user's palm during use may be overmolded with a thermoplastic elastomer or other resilient material to further increase comfort to a user. Materials other than those noted above can be used including metal, wood, or any other desired material that has sufficient structural rigidity to permit a user to grip the handle 302 and manipulate the oral care implement 300 during toothbrushing.

The head 303 is coupled to the handle 302 and has a front surface 304 and an opposing rear surface 305. In the exemplified embodiment, the head 303 is formed integrally with the handle 302 as a single unitary structure using a molding, milling, machining, or other suitable process. However, in other embodiments the handle 302 and the head 303 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Thus the head 303 may, in certain embodiments, be formed of any of the rigid plastic materials described above as being used for forming the handle 302, although the invention is not to be so limited in all embodiments and other materials that are commonly used during toothbrush head manufacture may also be used.

The oral care implements 300 comprise a plurality of tooth cleaning elements 306 extending from the front surface 304 of the head 303. It should be appreciated that the term "tooth cleaning elements" may be used in a generic sense to refer to any structure that can be used to clean, polish, or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof, and/or structures containing such materials or combinations. Thus, any combination of these tooth cleaning elements may be used within the tooth cleaning elements 306 in some embodiments.

In embodiments that use elastomeric elements as one or more of the tooth cleaning elements 306, suitable elastomeric materials may include any biocompatible resilient material suitable for uses in an oral hygiene apparatus. To provide optimum comfort as well as cleaning benefits, the elastomeric material of any such tooth or soft tissue engaging elements may have a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

Furthermore, in certain embodiments a soft tissue cleanser may be positioned on the rear surface 305 of the head 303 (a soft tissue cleanser is illustrated in the drawings). An example of a suitable soft tissue cleanser that may be used with the present invention and positioned on the rear surface of the head 303 is disclosed in U.S. Pat. No. 7,143,462, issued Dec. 5, 2006 to the assignee of the present application, the entirety of which is hereby incorporated by reference. In certain other embodiments, the soft tissue cleanser may include protuberances, which can take the form of elongated ridges, nubs, or combinations thereof. Of course, the invention is not to be so limited and in certain embodiments the oral care implements 300 may not include any soft tissue cleanser.

Referring to FIGS. 1, 4, 6, and 9-12 concurrently, the packaged oral care implement 1000 will be further described with particular discussion of the relationship between the various components of the packaged oral care implement 1000. Either after the insert tray 150 is positioned within the retaining section 121 of the blister carton 110 or before, the one or more oral care implements 300 are coupled to the insert tray 150. Specifically, each of the product receiving channels 157, 158 of the insert tray 150 is sized and shaped to hold and retain a portion of the handle 302 of the oral care implement 300 therein. Thus, a portion of a first one of the oral care implements 300 can be snap-fit (or otherwise disposed such as via interference fit, sliding engagement, fasteners, or the like) into the first product receiving channel 157 and a portion of a second one of the oral care implements 300 can be snap-fit (or otherwise disposed such as via interference fit, sliding engagement, fasteners, or the like) into the second product receiving channel 158. Of course, as noted above one oral care implement 300 or more than two oral care implements 300 can be positioned within each package 100 in other embodiments by adding or reducing the number of product receiving channels that are formed into the insert tray 150. When a portion of the oral care implements 300 is positioned within one of the product receiving channels 157, 158, the insert tray 150 prevents movement of the oral care implement 300 relative to the insert tray 150. FIG. 10 best illustrates the positioning of the oral care implements 300 within the product receiving channels 157, 158 of the insert tray 150.

It is possible to place the insert tray 150 within the receiving trough 116 first, and to then insert the one or more oral care implements 300 into the product receiving channels 157, 158 of the insert tray 150 because the product receiving channels 157, 158 of the insert tray 150 are facing the open rear end 117 of the blister carton 110. Thus, even with the insert tray 150 positioned within the receiving trough 116, there is access to the product receiving channels 157, 158 for mounting the oral care implements 300 to the insert tray 150.

When the oral care implements 300 are positioned within the product receiving channels 157, 158 of the insert tray 150, a middle portion 312 of the ansate body 301, and specifically of the handle 302, is positioned within the respective product receiving channel 157, 158 of the insert tray 150. When so positioned, a proximal portion 310 of the oral care implement 300 extends beyond the lower end 155 of the insert tray 150 in a first axial direction (i.e., in the direction of the second lateral wall 114) and a distal portion 311 of the oral care implement 300 extends beyond the upper end 156 of the insert tray 150 in a second axial direction that is opposite to the first axial direction (i.e., in the direction of the first lateral wall 113). Thus, the insert tray 150 is only directly coupled to a small portion of the oral care implement 300 (i.e., the middle portion 312), and thus the insert tray 150 does not take up a significant amount of space within the receiving trough 116. The proximal portion 310 of the ansate body 301 of the oral care implement 300 is positioned within the lower axial section 118 of the receiving trough 116, the middle portion 312 of the ansate body 301 of the oral care implement 300 is positioned within the middle axial section 118 of the receiving trough 116, and the distal portion 311 of the ansate body 301 of the oral care implement 300, which includes the head 303 of the oral care implement 300, is positioned within the upper axial section 120 of the receiving trough 116. In the exemplified embodiment, the head 303 of the oral care implement 300 is located entirely within the upper axial section 120 of the receiving trough 116.

Although described herein as the middle portion 312, in certain embodiments the middle portion 312 is not centrally located on the ansate body 301, but rather is a portion of the ansate body 301 that does not form an end of the ansate body 301. Thus, the ansate body 301 has a proximal portion 310 and a distal portion 311 that are on opposing sides of the middle portion 312, and the middle portion 312 may be any section of the ansate body 301 that is located between two other sections of the ansate body 301. Furthermore, although described herein such that the middle portion 312 is positioned within the product receiving channels 157, 158 of the insert tray 150, in other embodiments the proximal 310 or distal 311 portions of the ansate body 301 may be positioned within the product receiving channels 157, 158 of the insert tray 150. In such embodiments, a portion of the ansate body 301 may extend beyond one of the upper and lower ends 155, 156 of the insert tray 150, but not both.

After the insert tray 150 and the oral care implement(s) 300 are positioned within the receiving trough 116, the backer panel 180 is coupled to the open rear end 117 of the blister carton 110 to enclose the receiving trough 116. The backer panel 180 may be coupled to the open rear end 117 of the blister carton 110 via adhesion, fasteners, thermal fusion, or the like. Specifically, the open rear end 117 of the blister carton 110 is defined by/surrounded by a lip/flange 147 (FIG. 6) to which the backer panel 180 can be coupled in any of the manners noted above.

In certain embodiments, the backer panel 180 may be formed from an opaque cellulosic material, such as a cardboard, paperboard, paper stock, or the like. Of course, the invention is not to be so limited and the backer panel 180 may be formed of transparent or translucent materials, and the backer panel 180 may be formed of materials other than cellulosic material, such as plastics or the like, in other embodiments. The backer panel 180 has a front surface 181 and a rear surface 182. In certain embodiments, each of the front and rear surfaces 181, 182 of the backer panel 180 may include text, indicia, patterned coloring, instructions, graphics, or the like. As noted above, due to the small size of the insert tray 150, the insert tray 150 does not block the view of most of the front surface 181 of the backer panel 180 so that graphics, text, instructions, and the like printed onto the front surface 181 of the backer panel 180 remains clearly visible to the consumer.

In the assembled packaged oral care implement 1000, the oral care implement 300 is oriented so that the front surface 304 of the head 303 and the tooth cleaning elements 306 face the front wall 115 of the blister carton 110 and the rear surface 305 of the head 303 faces the front surface 181 of the backer panel 180. Furthermore, the insert tray 150 is positioned in between the oral care implement(s) 300 and the front wall 115 of the blister carton 110, and the oral care implement(s) 300 are positioned between the insert tray 150 and the backer panel 180. In the exemplified embodiment, the oral care implement(s) 300 are entirely spaced apart from the front wall 115 of the blister carton 110. Thus, no portion of the ansate body 301 of the oral care implements 300 contacts the front wall 115 of the blister carton 110. Furthermore, in the exemplified embodiment the rear surface of portions of the handle 302 of the oral care implement 300 are in surface contact with the front surface 181 of the backer panel 180. However, in other embodiments no portion of the ansate body 301 of the oral care implements 300 contacts the backer panel 180. In such embodiments, the oral care implements 300 may be entirely retained within the receiving trough 116 by the insert tray 150 and the oral care implement 300 may appear to be floating with the receiving trough 116 when viewed by a consumer.

Furthermore, as has been discussed above, the label 101 is positioned atop of the front retaining portion 130 of the front wall 115 of the blister carton 110. In embodiments in which the label 101 is opaque, the label 101 at least partially, and in some embodiments entirely, conceals the insert tray 150 when viewed through the front wall 115. Thus, in certain embodiments the label 101 completely conceals the insert tray 150 such that no portion of the insert tray 150 is visible when viewed from a front of the blister carton 110 through the front wall 115 of the blister carton 110. Thus, in certain embodiments the label 101, the front retaining portion 130 of the front wall 115, and the insert tray 150 have the same surface area and are positioned at the same location of the package so that any plane that is perpendicular to the longitudinal axis A-A and to the front wall 115 of the blister carton 110 that intersects the label 101 will also intersect the front retaining portion 130 and the insert tray 150. In other embodiments, the insert tray 150 may be slightly smaller in surface area than the label 101 and/or than the front retaining portion 130.

Figure 13:
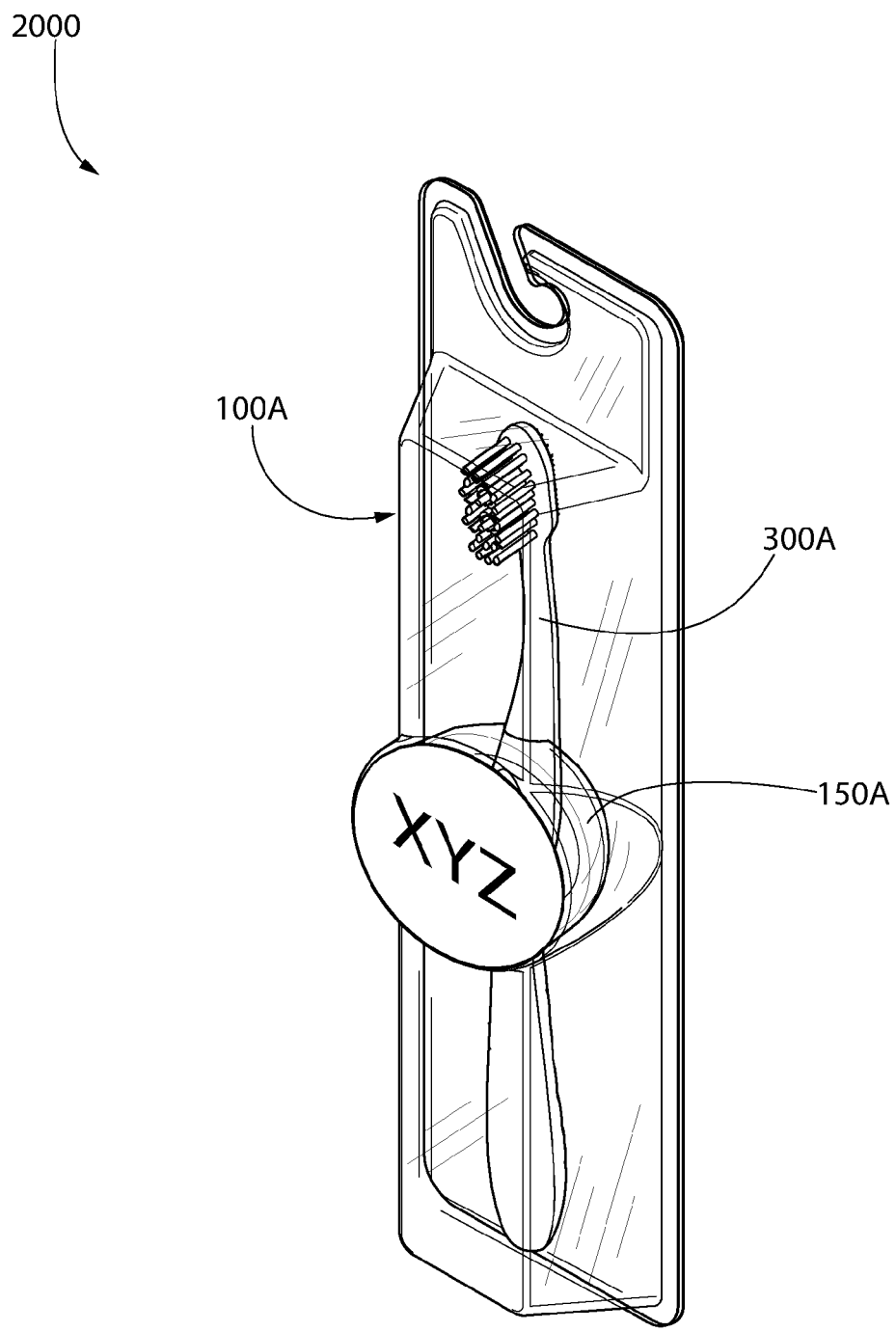
FIG. 13 is a front perspective view of a packaged oral care implement in accordance with a second embodiment of the present invention.

Referring briefly to FIG. 13, a packaged oral care implement 2000 is illustrated in accordance with an embodiment of the present invention. The packaged oral care implement 200 is identical to the packaged oral care implement 1000 except that there is only one oral care implement 300A positioned within the package 100A. Thus, in this embodiment the insert tray 150A only has one product receiving channel instead of two, and thus the package 100A only contains one oral care implement 300A. All other features of the packaged oral care implement 2000 are identical to those described above with regard to the packaged oral care implement 1000, and thus they will not be described in detail herein in the interest of brevity. Furthermore, although the drawings only depict embodiments with one or two oral care implements, in other embodiments the package may include three, four, five, or more oral care implements as desired utilizing the techniques described herein. Thus, the invention is not to be limited by the particular number of oral care implements that are retained within the package in all embodiments.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A packaged oral care implement comprising:
 a package comprising:
  a blister carton comprising a first longitudinal sidewall, a second longitudinal sidewall and a front wall extending between the first and second longitudinal sidewalls, wherein the first and second longitudinal sidewalls and the front wall collectively define a receiving trough, the receiving trough having an open rear end, the receiving trough extending along a longitudinal axis and comprising a lower axial section, a middle axial section, and an upper axial section, the middle axial section located between the lower and upper axial sections;

an insert tray positioned within the receiving trough and located entirely within the middle axial section of the receiving trough, the middle axial section comprising a front retaining portion in the front wall, a first side retraining portion in the first longitudinal sidewall and a second side retaining portion in the second longitudinal sidewall, the insert tray retained in a fixed axial position relative to the blister carton through mating with the front retaining portion, the first side retaining portion and the second side retaining portion, the insert tray comprising a first product receiving channel; and a backer panel coupled to the blister carton that encloses the open rear end of the receiving trough; and a first oral care implement having an ansate body positioned within the receiving trough of the blister carton, a portion of the ansate body positioned within the first product receiving channel of the insert tray to prevent movement of the first oral care implement relative to the insert tray.

2. The packaged oral care implement according to claim 1 wherein the first longitudinal sidewall comprises a first planar section and a second planar section, the first side retaining portion located between the first and second planar sections of the first longitudinal sidewall; and wherein the second longitudinal sidewall comprises a first planar section and a second planar section, the second side retaining portion located between the first and second planar sections of the second longitudinal sidewall.

3. The packaged oral care implement according to claim 1 wherein the first side retaining portion of the first longitudinal sidewall comprises a first curved wall section having a concave inner surface and a convex outer surface, the first side portion of the insert tray nesting within the first curved wall section; and wherein the second side retaining portion of the second longitudinal sidewall comprises a second curved wall section having a concave inner surface and a convex outer surface, the second side portion of the insert tray nesting within the second curved wall section.

4. The packaged oral care implement according to claim 3 wherein the convex outer surface of the first curved wall section outwardly protrudes from the first and second planar sections of the first longitudinal sidewall; and wherein the convex outer surface of the second curved wall section outwardly protrudes from the first and second planar sections of the second longitudinal sidewall.

5. The packaged oral care implement according to claim 1 wherein the insert tray further comprises a middle portion located between the first and second side portions of the insert tray, the first product receiving channel located in the middle portion.

6. The packaged oral care implement according to claim 1 wherein the front retaining portion comprises a detent in an inner surface of the front wall, a rear portion of the insert tray nesting within the detent.

7. The packaged oral care implement according to claim 1 wherein the package further comprises a label overlying the front retaining portion and at least partially concealing the insert tray.

8. The packaged oral care implement according to claim 1 wherein the front wall comprises a first planar section and a second planar section, the front retaining portion located between the first and second planar sections of the front wall.

9. The packaged oral care implement according to claim 1 wherein the package further comprises a label on the front wall overlying the retaining section of the blister carton to at least partially conceal the insert tray.

10. The packaged oral care implement according to claim 1 wherein the insert tray comprises an upper end and a lower end, the first product receiving channel extending between the upper and lower ends; wherein a middle portion of the ansate body is positioned within the first product receiving channel of the insert tray; and wherein the ansate body comprises a proximal portion that extends beyond the lower end of the insert tray in a first axial direction and a distal portion that extends beyond the upper end of the insert tray in a second axial direction opposite the first axial direction.

11. The packaged oral care implement according to claim 1 wherein the backer panel is formed from an opaque cellulosic material, the blister carton is formed from a transparent plastic material, and the insert tray is formed of a transparent plastic material.

12. The packaged oral care implement according to claim 1 wherein no portion of the ansate body of the first oral care implement contacts the front wall of the blister carton.

13. The packaged oral care implement according to claim 1 wherein no portion of the insert tray is located in the upper and lower axial sections of the receiving trough; and wherein the middle axial section is less than 50% of a length of the receiving trough, the lower axial section is greater than 25% of the length of the receiving trough, and the upper axial section is greater than 25% of the length of the receiving trough.

14. The packaged oral care implement according to claim 1, further comprising:
a second product receiving channel in the insert tray; and
a second oral care implement having an ansate body positioned within the receiving trough of the blister carton, a portion of the ansate body of the second oral care implement positioned within the second product receiving channel to prevent movement of the second oral care implement relative to the insert tray.

15. A packaged oral care implement comprising:
a package comprising:
a blister carton comprising a receiving trough having an open rear end, the receiving trough extending along a longitudinal axis, the blister carton comprising a first longitudinal sidewall, a second longitudinal sidewall and a front wall extending between the first and second longitudinal sidewalls, wherein the first and second longitudinal sidewalls and the front wall collectively define the receiving trough, the receiving trough comprising a front retaining portion in the front wall, a first side retraining portion in the first longitudinal sidewall and a second side retaining portion in the second longitudinal sidewall;
an insert tray positioned within the receiving trough, the insert tray comprising a first product receiving channel extending between upper and lower ends of the insert tray; and
a backer panel coupled to the blister carton that encloses the open rear end of the receiving trough; and
a first oral care implement comprising an ansate body positioned within the receiving trough of the blister carton, a middle portion of the ansate body of the first oral care implement positioned within the first product receiving channel of the insert tray so that a proximal portion of the ansate body extends beyond the lower end of the insert tray in a first axial direction and a distal portion of the ansate body extends beyond the upper end of the insert tray in a second axial direction opposite the first axial direction, wherein the insert tray is retained in a fixed axial position relative to the blister carton through mating with the front retaining portion, the first side retaining portion and the second side retaining portion of the blister carton; and wherein the ansate body is retained by the insert tray to prevent movement of the first oral care implement relative to the insert tray.

* * * * *